United States Patent
Trubey et al.

(10) Patent No.: US 10,571,445 B2
(45) Date of Patent: Feb. 25, 2020

(54) FIELDED CHEMICAL THREAT DETECTORS

(71) Applicant: Hamilton Sundstrand Corporation, Charlotte, NC (US)

(72) Inventors: Richard K. Trubey, Upland, CA (US); Hsien-Chi W. Niu, Rowland Heights, CA (US)

(73) Assignee: Hamilton Sundstrand Corporation, Charlotte, NC (US)

( * ) Notice: Subject to any disclaimer, the term of this patent is extended or adjusted under 35 U.S.C. 154(b) by 201 days.

(21) Appl. No.: 15/595,117

(22) Filed: May 15, 2017

(65) Prior Publication Data

US 2019/0011417 A1  Jan. 10, 2019

(51) Int. Cl.
*G01N 33/00* (2006.01)

(52) U.S. Cl.
CPC ..... *G01N 33/0057* (2013.01); *G01N 33/0062* (2013.01); *G01N 33/0073* (2013.01); *G01N 2033/0068* (2013.01)

(58) Field of Classification Search
CPC ........... G01N 33/0057; G01N 33/0062; G01N 33/0068; G01N 33/0073
See application file for complete search history.

(56) References Cited

U.S. PATENT DOCUMENTS

| | | | | |
|---|---|---|---|---|
| 3,852,730 A * | 12/1974 | Commins | .......... | G01N 33/0062 340/870.05 |
| 5,157,261 A * | 10/1992 | Grey | .................... | G01N 21/643 250/227.18 |
| 5,364,795 A * | 11/1994 | Sausa | ................... | G01N 21/631 250/461.1 |
| 5,728,584 A * | 3/1998 | Sausa | ................... | G01N 21/631 250/282 |
| 5,866,430 A * | 2/1999 | Grow | ..................... | G01N 21/65 436/172 |
| 7,057,721 B2 * | 6/2006 | Gardner, Jr. | .............. | G01J 3/02 356/301 |
| 7,333,190 B1 * | 2/2008 | Pendell-Jones | ....... | G01J 3/4406 250/461.1 |
| 7,391,557 B1 * | 6/2008 | Bruch | ....................... | G01J 3/10 356/450 |
| 7,436,515 B2 * | 10/2008 | Kaye | ..................... | G01J 3/4406 356/436 |
| 7,511,809 B2 * | 3/2009 | Schneider | ............ | G01N 1/2273 356/301 |
| 7,834,320 B2 * | 11/2010 | Goldberg | ............... | G01N 21/78 250/338.5 |
| 7,837,844 B2 | 11/2010 | Patel et al. | | |

(Continued)

FOREIGN PATENT DOCUMENTS

WO    WO-2014113106 A2 *  7/2014  ............. G01N 33/52

*Primary Examiner* — David J Bolduc
(74) *Attorney, Agent, or Firm* — Locke Lord LLP; Scott D. Wofsy; Joshua L. Jones

(57) ABSTRACT

A method for detecting chemical vapors includes acquiring an environmental air sample within at least one fielded chemical detector, detecting that at least one chemical from a selected set of possible chemicals is present within the environmental air sample, analyzing data relating to the detecting, determining at least one of a chemical name, a chemical concentration, a chemical category, or a toxicity level, and transmitting the determined information to a central data collection site.

14 Claims, 5 Drawing Sheets

(56) References Cited

U.S. PATENT DOCUMENTS

| | | | |
|---|---|---|---|
| 7,843,356 B2 | 11/2010 | Webb | |
| 7,965,089 B2 | 6/2011 | Bonne et al. | |
| 7,968,054 B1 * | 6/2011 | Li | G01N 27/127 422/68.1 |
| 7,993,585 B2 * | 8/2011 | Black | G01N 15/1463 422/82.05 |
| 8,618,934 B2 | 12/2013 | Belov et al. | |
| 8,994,546 B2 | 3/2015 | Breed et al. | |
| 9,103,775 B2 | 8/2015 | Bradley et al. | |
| 9,255,920 B1 * | 2/2016 | Lamberti | G01N 33/0057 |
| 9,429,522 B2 * | 8/2016 | Swager | C07F 15/0086 |
| 9,683,981 B1 * | 6/2017 | Vilkov | G01N 33/227 |
| 9,689,857 B1 * | 6/2017 | Vilkov | G01N 33/227 |
| 2004/0135684 A1 * | 7/2004 | Steinthal | B82Y 30/00 340/522 |
| 2004/0220753 A1 * | 11/2004 | Tabe | G01N 33/0057 702/32 |
| 2005/0039515 A1 * | 2/2005 | Prince | G01N 33/0057 73/1.06 |
| 2005/0230615 A1 * | 10/2005 | Furutani | B82Y 10/00 250/287 |
| 2005/0263694 A1 * | 12/2005 | Hayek | H01J 49/0036 250/287 |
| 2006/0188399 A1 * | 8/2006 | Smid | G01N 29/12 422/82.02 |
| 2008/0085212 A1 * | 4/2008 | Adams | G01N 29/036 422/50 |
| 2008/0088434 A1 * | 4/2008 | Frieder | G08B 21/12 340/539.11 |
| 2008/0195329 A1 * | 8/2008 | Prince | G01N 33/0062 702/23 |
| 2008/0311882 A1 * | 12/2008 | Schlager | A61N 1/08 455/404.2 |
| 2009/0115605 A1 * | 5/2009 | Ravenis | G01N 27/126 340/540 |
| 2010/0000882 A1 * | 1/2010 | Wang | G01N 33/0057 205/781 |
| 2010/0268480 A1 * | 10/2010 | Prince | G01N 1/26 702/24 |
| 2011/0045517 A1 * | 2/2011 | Derringer | C12Q 1/46 435/20 |
| 2011/0127421 A1 * | 6/2011 | Finlay | G01N 30/72 250/283 |
| 2012/0004851 A1 * | 1/2012 | Potyrailo | G01N 33/0073 702/19 |
| 2012/0038908 A1 * | 2/2012 | Beckstead | G01J 3/02 356/72 |
| 2012/0122075 A1 * | 5/2012 | Call | B01D 45/04 435/3 |
| 2012/0143515 A1 * | 6/2012 | Norman | G01N 33/0073 702/24 |
| 2012/0270205 A1 * | 10/2012 | Patel | G01N 27/126 435/5 |
| 2013/0115705 A1 * | 5/2013 | Patolsky | G01N 27/4146 436/106 |
| 2014/0281479 A1 * | 9/2014 | Gettings | G01N 33/0062 713/150 |
| 2015/0022357 A1 * | 1/2015 | Gettings | G01N 21/84 340/568.1 |
| 2016/0202222 A1 * | 7/2016 | Roberts | G01N 1/2202 435/5 |
| 2016/0282321 A1 * | 9/2016 | Syage | H01J 49/10 |
| 2017/0191973 A1 * | 7/2017 | Eusebi | G01N 33/0075 |
| 2017/0248514 A1 * | 8/2017 | Pavey | G01N 33/0057 |
| 2018/0174423 A1 * | 6/2018 | Trubey | G08B 21/12 |
| 2018/0196101 A1 * | 7/2018 | Qu | G01R 31/2829 |
| 2018/0217085 A1 * | 8/2018 | Braun | C12Q 1/44 |
| 2018/0231514 A1 * | 8/2018 | Kim | G01N 33/0057 |

* cited by examiner

FIELDED CHEMICAL THREAT DETECTORS

BACKGROUND OF THE INVENTION

1. Field of the Invention

The present disclosure relates to chemical detection, and more particularly to fielded chemical threat detectors which remain in the field to provide alerts and/or information regarding chemical threats.

2. Description of Related Art

Chemical threat detection generally relates to the recognition of and alert to of any number of known toxic chemical vapors in the environmental background. Military and homeland security applications include the detection of chemical warfare agents, toxic industrial chemicals, explosives, and illicit drugs used by enemy states or terrorists to intentionally harm military troops or civilians abroad or in the U.S. The ability to detect toxic chemicals is important in a variety of other contexts, including the detection of potentially toxic chemicals in factory or on the grounds of a chemical plant, petroleum refinery, entry port, or railroad yard to prevent fire, injury, death, or health problems. The early detection of chemical agent precursors and toxic chemical vapors in general may provide an opportunity to warn military personnel or the public in sufficient time to provide an opportunity for appropriate preventative actions, personal protection by donning protective equipment, or containment of the chemical threat source.

Typical chemical threat detectors are heavy, complex, and consume too much power to be deployed as a network of autonomous fielded detectors. However, such a network could be used by environmental regulators to continuously monitor emissions from large industrial installations. Emergency response teams could use such a network to monitor toxic chemical releases into the air following a major industrial transportation accident. The government could use such a network to provide early warning of a chemical warfare attack on troops as well as for use for covert surveillance operations.

The conventional techniques have been considered satisfactory for their intended purpose. However, there is an ever present need for improved fielded chemical threat detectors. This disclosure provides a solution for this need.

SUMMARY OF THE INVENTION

A method for detecting airborne chemicals includes acquiring an environmental air sample within at least one fielded chemical detector, detecting that at least one chemical from a selected set of possible chemicals is present within the environmental air sample, analyzing data relating to the detecting, determining information including at least one of a chemical name, a chemical concentration, a chemical category, or a toxicity level, and transmitting the determined information to a central data collection site.

The method can include staggering turning on/off of sampling and detecting components to conserve power by not powering components that are not in use. The method includes placing the at least one fielded chemical detector into a sleep mode for power conservation and waking the at least one fielded chemical detector from the sleep mode for the acquiring, detecting, analyzing, determining, and transmitting. Placing the at least one fielded chemical detector into a sleep mode and waking the at least one fielded detector from the sleep mode includes periodically placing the at least one fielded chemical detector into a sleep mode and waking the at least one fielded chemical detector on a predetermined schedule. An environmental air sample can be acquired each time the at least one fielded chemical detector is woken out of the sleep mode.

Placing the at least one fielded chemical detector into a sleep mode and waking the at least one fielded detector from the sleep mode can include waking the at least one fielded chemical detector into a partially powered mode periodically, wherein the partially powered mode includes powering on a communication module without acquiring an environmental air sample to monitor for a command to fully wake up the at least one fielded chemical detector from the sleep mode. Powering on a communication module without acquiring an environmental air sample can include returning the at least one fielded chemical detector to the sleep mode without acquiring an environmental air sample if the communication module does not receive a command to fully wake up the at least one fielded chemical detector, or fully waking the at least one fielded chemical detector if the communication module received a command to fully wake up the at least one fielded chemical detector, and thereafter acquiring the environmental air sample. Monitoring for a command to fully wake up includes monitoring for a command signal from at least one of another fielded chemical detector or a main controller.

The method can include triangulating a location of a source of the at least one detected chemical from a plurality of fielded chemical detectors. The method can include using aggregated data from a plurality of fielded chemical detectors to perform at least one of creating a chemical concentration map of the at least one detected chemical, and/or forecasting movement of the at least one detected chemical. Aggregated data from a plurality of fielded chemical detectors can be used to determine whether an alert of one or more detected chemicals present is a false positive. The method can include repeating the acquiring, detecting, analyzing, determining, and transmitting until one or more detected chemicals are no longer detected. The method can include repeating the acquiring, detecting, analyzing, determining, and transmitting intermittently in an operation with a duration of a plurality of months without replenishing consumables or performing maintenance action.

A fielded chemical vapors detecting system at least one fielded chemical detector, each including a housing. A gas sampling device is disposed within the housing. A sensor is operatively connected to the gas sampling device. A power management system is disposed within the housing and is operatively connected to the sensor. A controller is operatively connected to the sensor. The controller includes a processor and a memory integrated circuit (IC) storing instructions that, when executed by the processor, cause the system to acquire an environmental air sample within the gas sampling device, electronically monitor the sensor for current and/or voltage changes, detect via the electronic monitoring that at least one chemical of a selected set of chemicals is present within the environmental air sample, determine at least one of a chemical name, a chemical concentration, a chemical category, or a toxicity level, and transmit the determined information to a central data collection site.

The sensor can include an ion mobility spectrometer or tandem ion mobility spectrometer which includes two ion mobility spectrometers and an ion fragmentation stage. A pump can be included for circulating the environment air sample into and out of the gas sampling device. The system can include instructions to cause the system to perform any of the methods described above.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
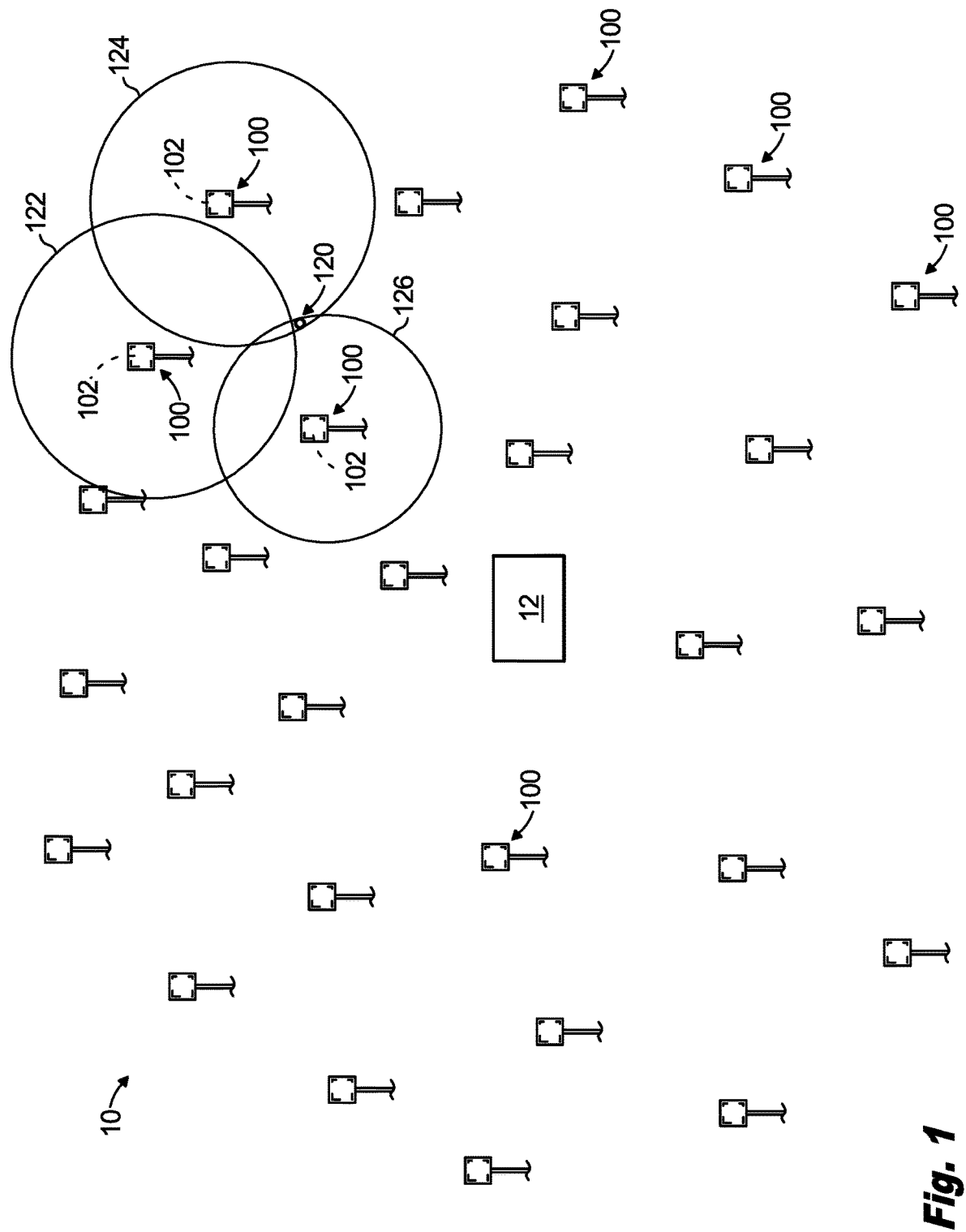
FIG. 1 is a schematic view of an exemplary embodiment of a system of fielded networked chemical threat detectors, showing the main controller aggregating data to locate a chemical threat.

Reference will now be made to the drawings wherein like reference numerals identify similar structural features or aspects of the subject disclosure. For purposes of explanation and illustration, and not limitation, a partial view of an exemplary embodiment of a system in accordance with the disclosure is shown in FIG. 1 and is designated generally by reference character 10. Other embodiments of the system in accordance with the disclosure, or aspects thereof, are provided in FIGS. 2-5, as will be described. The systems and methods described herein can be used to provide a network of fielded chemical threat detectors for long term operation without replacing consumables such as power sources and without needing maintenance.

Figure 2:
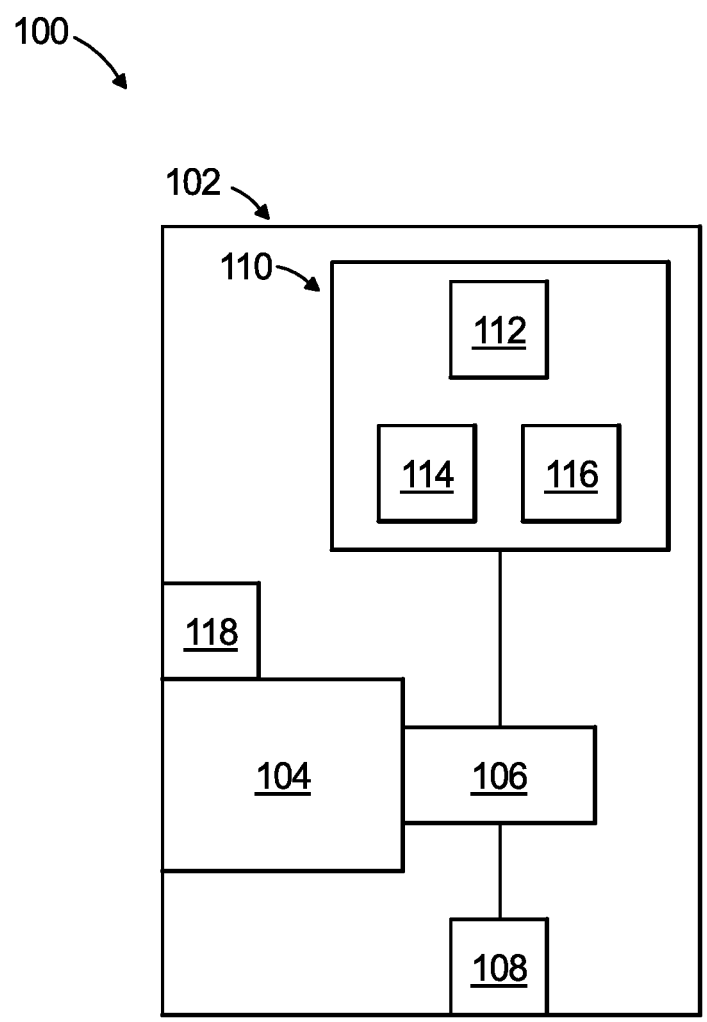
FIG. 2 is a schematic view of one of the chemical threat detectors of FIG. 1, showing the housing with components disposed therein.

System 10 includes a main controller 12 networked with a plurality of fielded, chemical vapors threat detectors 100, only a few of which are identified by reference character in FIG. 1 for the sake of clarity. With reference to FIG. 2, each chemical threat detector 100 includes a housing 102. A gas sampling device 104 is disposed within the housing 102. A sensor 106 is operatively connected to the gas sampling device 104. A power management system 108 is disposed within the housing 102 and is operatively connected to the sensor 106. A controller 110 is operatively connected to the sensor 106. The controller includes a processor 112 and a communication module 116 for input/output. A memory integrated circuit (IC) 114 in included in the controller 112 for storing instructions that, when executed by the processor 112, cause the system 10 to acquire an environmental air sample within the gas sampling device 104, electronically monitor the sensor 106 for changes in electrical current and/or voltage, detect via the electronic monitoring that at least one chemical of a selected set of chemicals is present within the environmental air sample, determine at least one of a chemical name, a chemical concentration, a chemical category, or a toxicity level, and transmit the determined information to a central data collection site, e.g., main controller 12 of FIG. 1. The instructions can include instructions to cause the system 10 to perform any of the methods described herein.

Figure 3:
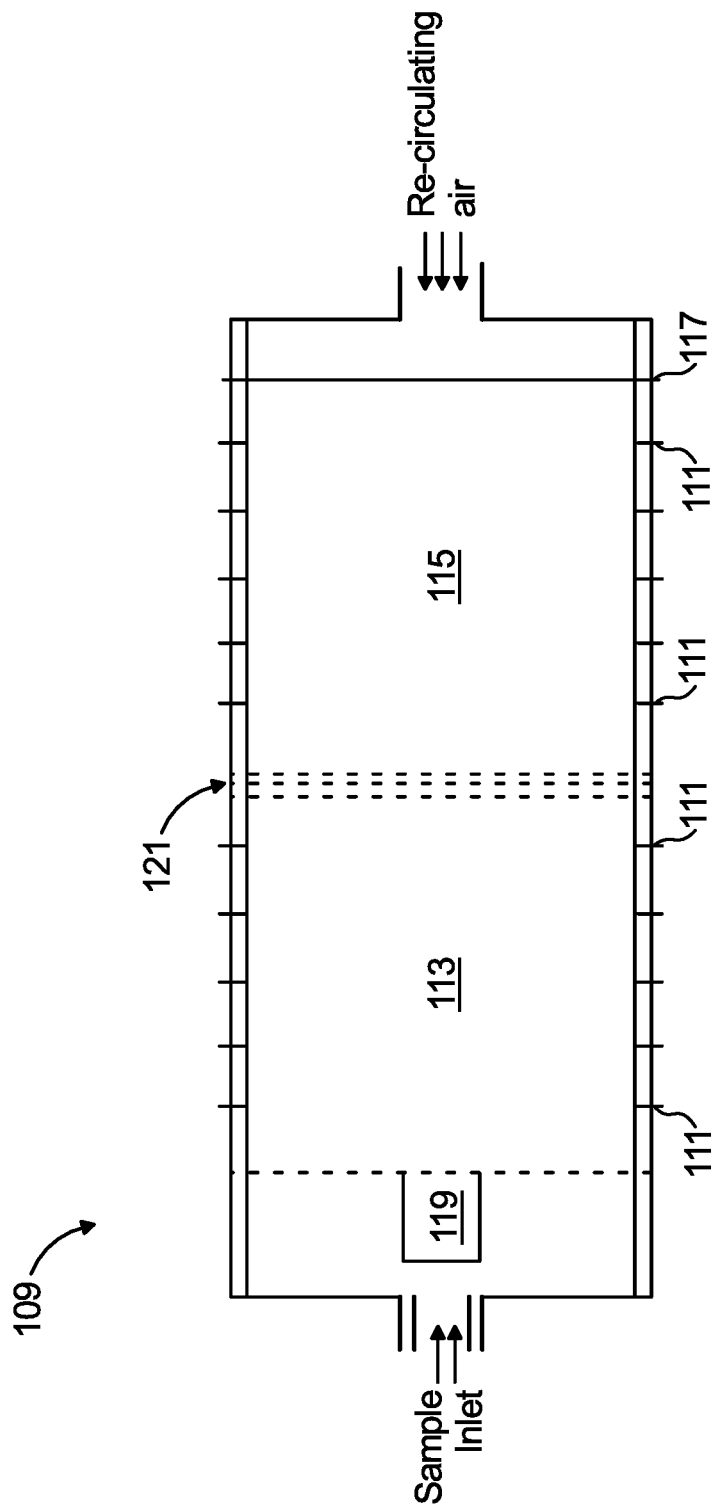
FIG. 3 is a schematic view of an exemplary sensor for use in the detector of FIG. 1.

With reference now to FIG. 3, the sensor 106 can include an ion mobility or tandem-ion mobility spectrometer device 109. Ions can be created from the environment air sample by means of a radioactive foil 119 containing Nickel-63. Ions are propelled through the focusing rings 111 due to a linear electric field generated by applying an electrical potential to the focusing rings 111. This scheme requires that each focusing ring 111 be charged to a voltage that differs uniformly (e.g., 100 V) from the voltage of the adjacent focusing ring 111. Ions are separated according to their molecular size and structure in a first drift tube 113. The separated ions are isolated and enter into the ion fragmentation stage 121 where they are excited and fragmented. The fragmented ions are further separated by the second drift tube 115 and are detected using a Faraday collector 117 located to the right of the second drift tube 115 in FIG. 3. This tandem arrangement enhances the selectivity. A pump 118, shown in FIG. 1, can be included for circulating the environment air sample into and out of the gas sampling device 104. This pump 118 can also be used to circulate clean air through the focusing rings 111 to cause the ion separation described earlier. The sensor 106 can include an ion mobility spectrometer or a tandem ion mobility spectrometer which includes two ion mobility spectrometers and an ion fragmentation stage as described above.

With reference again to FIG. 1, a method for detecting airborne chemicals includes acquiring an environmental air sample within at least one fielded chemical detector, e.g. chemical detector 100, detecting that at least one chemical from a selected set of possible chemicals is present within the environmental air sample, analyzing data relating to the detecting, determining information including at least one of a chemical name, a chemical concentration, a chemical category, or a toxicity level, and transmitting the determined information to a central data collection site, e.g., main controller 12.

The method includes placing the fielded chemical detectors 100 into a sleep mode for power conservation and waking the chemical detectors 100 from the sleep mode for the acquiring, detecting, analyzing, determining, and transmitting described above. Placing the fielded chemical detectors 100 into a sleep mode and waking the fielded detectors 100 from the sleep mode can include periodically placing the fielded chemical detectors 100 into sleep mode and waking the fielded chemical detectors on a predetermined schedule. For example each chemical detector 100 can be programmed to wake every 12 hours, perform the routine of acquiring, detecting, analyzing, determining, and transmitting as described above, and then return to sleep mode. An environmental air sample can be acquired each time the fielded chemical detector 100 is woken out of the sleep mode. It should be noted that all of the fielded chemical detectors 100 of system 10 can be on the same sleep mode/wake up cycle, it can be advantageous for them to be out of sync so that threats arising during the sleep mode of one chemical detector 100 can be detected by a neighboring chemical detector 100 that wakes up out of sync with the first. This way, in the example of only waking every 12 hours, it is not necessary to wait up to 12 hours to detect a chemical presence.

In another example, placing the fielded chemical detectors 100 into a sleep mode and waking them from the sleep mode can include waking the fielded chemical detectors 100 into a partially powered mode periodically. The partially powered mode includes powering on the communication module 116 without acquiring an environmental air sample. This allows the chemical detectors 100 to briefly monitor for a command, e.g., from another chemical detector 100 or from the main controller 12, to fully wake up from the sleep mode. This can include returning the chemical detector 100 to the sleep mode without acquiring an environmental air sample if the communication module 116 does not receive a command to fully wake up, or fully waking from the partially powered mode if the communication module 116 received a command to fully wake up. Thereafter, the chemical detector 100 can perform the full routine of acquiring the environmental air sample described above. This preserves power for long term operation, since energy for acquiring an environmental air sample need not occur unless needed for at least some of the chemical detectors 100 in system 10.

Power management is of premium importance to efficiently minimize the energy per analysis. For low-level trace analysis, system equilibration is of importance to obtain reliable data. During the preparation stage when only the sample pump 118 is switched on, the controller 112 e.g., a microcontroller, should use only small amount of power. During the analysis period, all other electrical devices can be switched on according to when they are needed. For example, the fragmentation field can be pulsed, and the detector electronics need only be powered on during detection. The method can thus include staggering turning on/off of sampling and detecting components to conserve power by not powering components that are not in use.

With reference again to FIG. 1, the method can include triangulating a location of the source 120 of the at least one detected chemical determined from a plurality of fielded chemical detectors 100. For the three chemical detectors 100 identified with circles 122, 124, and 126 in FIG. 1, the distance from each chemical detector 100 to the source 120 can be inferred from the strength of reading the chemical(s) detected from the source 120. Aggregating the three distances, e.g., the radii of circles 122, 124, and 126, from each of the respective chemical detectors 100 to the source 120, and knowing the locations of the three chemical detectors 100, allows main controller 12 to determine the location of the source 120. Machine readable instructions for the data aggregation operations describe herein can reside in the main controller 12 and/or one or more of the chemical detectors 100.

Figure 4:
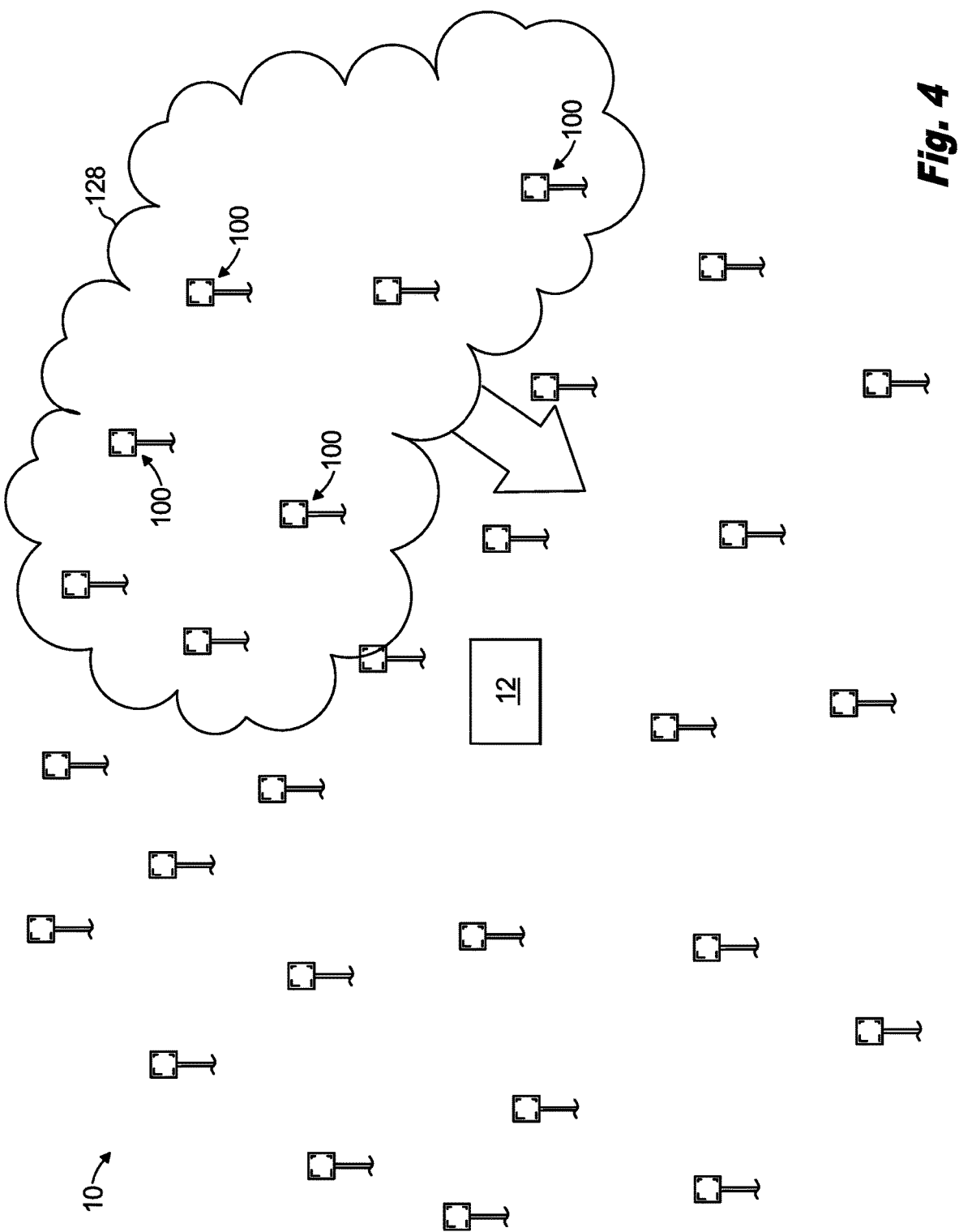
FIG. 4 is a schematic view of the system of FIG. 1, showing the main controller aggregating data to map and forecast movement of a chemical threat.
Figure 5:
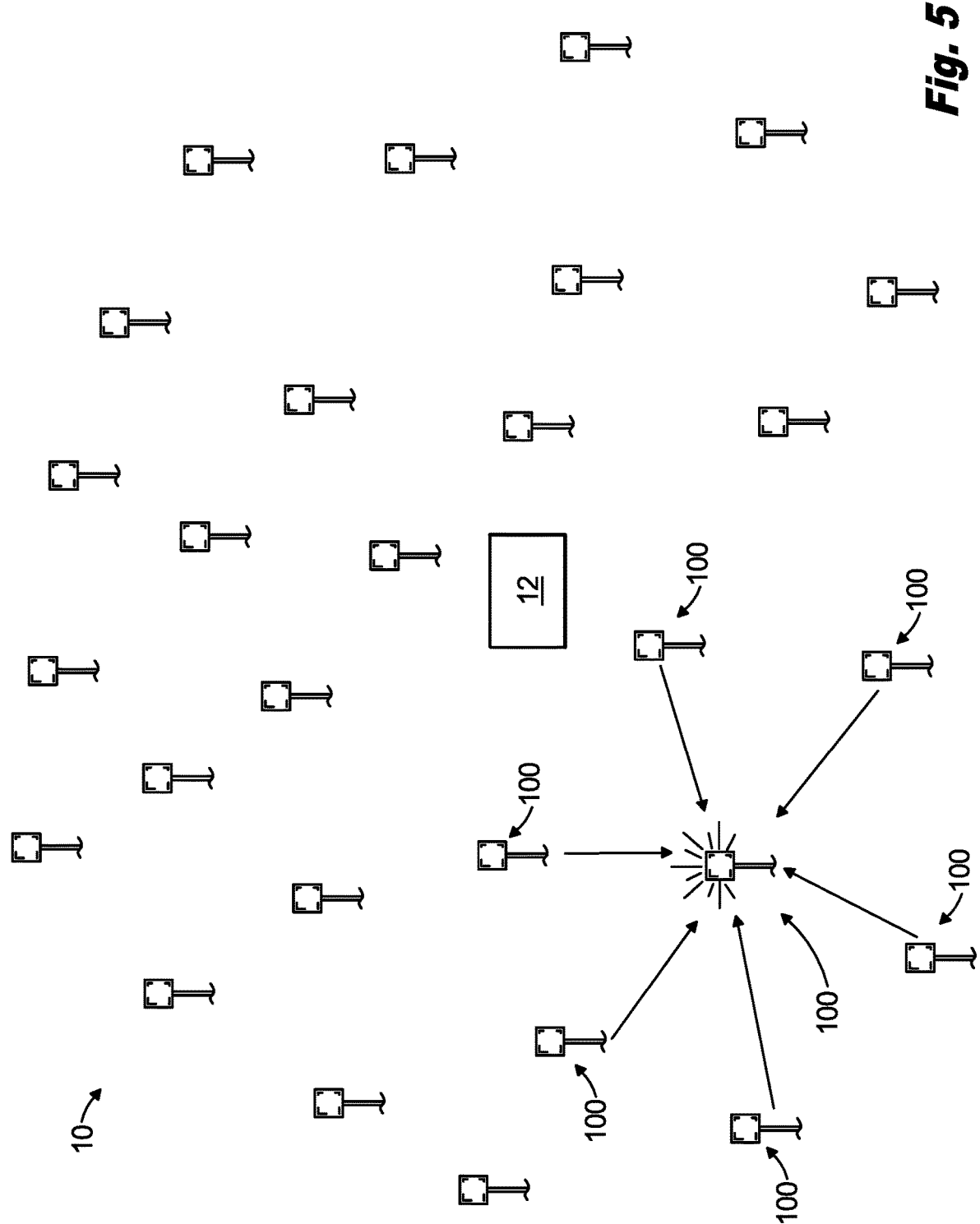
FIG. 5 is a schematic view of the system of FIG. 1, showing the main controller aggregating data to reject false positives.

With reference now to FIG. 4, the method can include using aggregated data from a plurality of fielded chemical detectors 100 to creating a chemical concentration map of the at least one detected chemical. For example, main controller 12 can aggregate data from the chemical detectors 100, including strength of reading the chemical(s) for each affected chemical detector 100, to map out the size and shape of a chemical presence, represented in FIG. 4 by a cloud 128. Aggregating data about the change in strength of reading the chemical(s) for each affected chemical detector 100 can allow main controller 12 to track and even forecast movement of the at least one detected chemical, e.g. cloud 128, as represented in FIG. 4 by the large arrow. The method can include repeating the acquiring, detecting, analyzing, determining, and transmitting until one or more detected chemicals are no longer detected.

Main controller 12 can also use aggregated data from a plurality of fielded chemical detectors 100 to determine whether an alert of one or more detected chemicals present is a false positive. For example, in FIG. 5 the chemical detector 100 denoted with radiating lines has indicated a positive reading for one or more chemical threats. Main controller 12 uses aggregated data from neighboring chemical detectors 100, as indicated by the inward pointing arrows in FIG. 5, to determine that the positive reading is a false positive because the surrounding chemical detectors 100 do not register any positives. This rejection technique allows for use of lower sensitivity sensors with lower weights and power consumption levels than would be required in the absence of such a false-positive rejection scheme. Furthermore, sensors using different detection schemes, e.g., mobility sensors and sensor arrays, can be networked together to further enhance the detection confidence.

The chemical detectors 100 can be connected wirelessly to main controller 12 and/or to each other, for example by satellite uplink, or any other suitable wired or wireless connection. The power management system 108 can include batteries, capacitors, and/or energy harvesters such as solar cells to provide long term operation without the need for power lines. This can provide for long term surveillance for indoor and/or outdoor use.

Due to the power management schemes, and the structure of the chemical detectors 100 described herein, the methods can allow repeating the acquiring, detecting, analyzing, determining, and transmitting intermittently in an operation with a duration of a plurality of months without replenishing consumables or performing maintenance action. Conventional chemical detectors are too large, heavy, and power-hungry to be suitable for use in a network of fielded chemical detectors. By reducing size, weight, and power consumption for the individual chemical detectors, the result is a system that can be suitable for fielded networks as described herein. The autonomous aspects of such a network can greatly reduce manpower costs for collecting the data manually. The networked capabilities lead to determination of location, severity, and behavior of chemical threat sources without needing to send people into harm's way.

The methods and systems of the present disclosure, as described above and shown in the drawings, provide for chemical threat detection with superior properties including long term fielded use of chemical threat detectors without replacement of consumables or maintenance. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A method for detecting chemical vapors, comprising:
   acquiring an environmental air sample within at least one fielded chemical detector;
   detecting that at least one chemical from a selected set of possible chemicals is present within the environmental air sample, wherein detecting includes using a tandem ion mobility spectrometer device which includes two ion mobility spectrometers and an ion fragmentation stage;
   analyzing data relating to the detecting;
   determining information including at least one of a chemical name, a chemical concentration, a chemical category, or a toxicity level; and
   transmitting the determined information to a data collection site.

2. The method as recited in claim 1, further comprising staggering turning on/off of sampling and detecting components to conserve power by not powering components that are not in use.

3. The method as recited in claim 1, further comprising triangulating a location of a source of the at least one detected chemical from a plurality of the at least one fielded chemical detectors.

4. The method as recited in claim 1, further comprising using aggregated data from a plurality of the at least one fielded chemical detectors to create a chemical concentration map of the at least one detected chemical.

5. The method as recited in claim 1, further comprising using aggregated data from a plurality of the at least one fielded chemical detectors to forecast movement of the at least one detected chemical.

6. The method as recited in claim 1, further comprising using aggregated data from a plurality of the at least one fielded chemical detectors to create a concentration map and forecast movement of the at least one detected chemical.

7. The method as recited in claim 1, further comprising using aggregated data from a plurality of the at least one fielded chemical detectors to determine whether an alert of one or more detected chemicals present is a false positive.

8. The method as recited in claim 1, further comprising repeating the acquiring, the detecting, the analyzing, the determining, and the transmitting until one or more detected chemicals are no longer detected.

9. The method as recited in claim 1, further comprising repeating the acquiring, the detecting, the analyzing, the determining, and the transmitting intermittently in an operation with a duration of a plurality of months without replenishing consumables or performing maintenance action.

10. A fielded chemical detecting system, comprising:
at least one fielded chemical detector, each comprising:
    a housing;
    a gas sampling device disposed within the housing;
    a sensor operatively connected to the gas sampling device, wherein the sensor of each of the at least one fielded chemical detectors comprises a tandem ion mobility spectrometer device which includes two ion mobility spectrometers and an ion fragmentation stage;
    a power management system disposed within the housing and operatively connected to the sensor; and
    a controller operatively connected to the sensor, comprising:
        a processor; and
        a memory integrated circuit (IC) storing instructions that, when executed by the processor, cause the system to:
acquire an environmental air sample within the gas sampling device;
electronically monitor the sensor for voltage and/or current changes;
detect via the electronic monitoring that at least one chemical of a selected set of chemicals is present within the environmental air sample;
determine at least one of a chemical name, a chemical concentration, a chemical category, or a toxicity level; and
transmit the determined information to a data collection site.

11. The system of claim 10, each of the at least one fielded chemical detectors further comprising a pump for circulating the environment air sample into and out of the gas sampling device.

12. The system as recited in claim 10, wherein the system includes instructions that cause the system to use aggregated data from a plurality of the at least one fielded chemical detectors to perform at least one of:
creating a chemical concentration map of the at least one detected chemical; and/or
forecasting movement of the at least one detected chemical.

13. The system as recited in claim 10, wherein the instructions include instructions that cause the system to use aggregated data from a plurality of fielded chemical detectors to determine whether an alert of one or more detected chemicals present is a false positive.

14. The system as recited in claim 10, wherein the instructions include instructions that cause the system to repeat acquiring, detecting, analyzing, determining, and transmitting intermittently in an operation with a duration of a plurality of months without replenishing consumables or maintenance action.

* * * * *